United States Patent
Watanabe (10) Patent No.: US 11,169,148 B2
(45) Date of Patent: Nov. 9, 2021

(54) METHOD FOR DETECTING TEST SUBSTANCE AND REAGENT KIT FOR DETECTING TEST SUBSTANCE

(71) Applicant: SYSMEX CORPORATION, Kobe (JP)

(72) Inventor: Toshihiro Watanabe, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 354 days.

(21) Appl. No.: 16/056,853

(22) Filed: Aug. 7, 2018

(65) Prior Publication Data
US 2018/0348212 A1    Dec. 6, 2018

Related U.S. Application Data

(63) Continuation of application No. PCT/JP2017/004271, filed on Feb. 6, 2017.

(30) Foreign Application Priority Data

Feb. 8, 2016  (JP) .............................. JP2016-021610

(51) Int. Cl.
*G01N 33/543*    (2006.01)

(52) U.S. Cl.
CPC . *G01N 33/54306* (2013.01); *G01N 33/54313* (2013.01); *G01N 2333/4709* (2013.01); *G01N 2800/2821* (2013.01)

(58) Field of Classification Search
CPC ... G01N 2333/4709; G01N 2800/2821; G01N 33/54306; G01N 33/54313
See application file for complete search history.

(56) References Cited

U.S. PATENT DOCUMENTS

| | | |
|---|---|---|
| 2010/0009388 A1 | 1/2010 | An et al. |
| 2010/0021943 A1 | 1/2010 | An et al. |
| 2011/0091910 A1 | 4/2011 | Kleinschmidt et al. |
| 2011/0104821 A1 | 5/2011 | Tokuda et al. |
| 2013/0052670 A1 | 2/2013 | Savage et al. |
| 2017/0030899 A1* | 2/2017 | Watanabe ............ G01N 33/544 |

FOREIGN PATENT DOCUMENTS

| | | |
|---|---|---|
| CN | 101124342 A | 2/2008 |
| CN | 101427132 A | 5/2009 |
| CN | 102612653 A | 7/2012 |
| CN | 104737020 A | 6/2015 |
| CN | 104969070 A | 10/2015 |
| EP | 0572217 A1 | 12/1993 |
| WO | 2006/088281 A1 | 8/2006 |
| WO | 2012/113718 A1 | 8/2012 |
| WO | 2014/074835 A2 | 5/2014 |

OTHER PUBLICATIONS

Ishikawa et al., "Ultrasensitive enzyme immunoassay," Clin. Chim. Acta, 1990, vol. 194, pp. 51-72.*

Asako Umehara et al: "A novel ultra-sensitive enzyme immunoassay for soluble human insulin receptor ectodomain and its measurement in urine from healthy subjects and patients with diabetes mellitus", Clinical Biochemistry, vol. 42, No. 13-14, Jun. 25, 2009, pp. 1468-1475; Cited in the extended European search report dated Jul. 19, 2019 in a counterpart European patent application.

Seiichi Hashida et al: "Development of an ultrasensitive enzyme immunoassay for human proadrenomedullin N-terminal 20 peptide and direct measurement of two molecular forms of PAMP in plasma from healthy subjects and patients with cardiovascular disease", Clinical Biochemistry, vol. 37, No. 1, 2004, pp. 14-21; Cited in the extended European search report dated Jul. 19, 2019 in a counterpart European patent application.

Satoshi Numata et al: "Development of a novel ultrasensitive enzyme immunoassay for human glutamic acid decarboxylase 65 antibody", Annals of Clinical Biochemistry, vol. 53, No. 4, Sep. 17, 2015, pp. 495-503; Cited in the extended European search report dated Jul. 19, 2019 in a counterpart European patent application.

Toshihiro Watanabe et al: "The immune complex transfer enzyme immunoassay: Mechanism of improved sensitivity compared with conventional sandwich enzyme immunoassay", Journal of Immunological Methods, vol. 459, Aug. 2018, pp. 76-80; Cited in the extended European search report dated Jul. 19, 2019 in a counterpart European patent application.

The extended European search report dated Jul. 19, 2019 in a counterpart European patent application 17750220.0.

E. Ishikawa et al., "Principle and Applications of Ultrasensitive Enzyme Immunoassay (Immune Complex Transfer Enzyme Immunoassay) for Antibodies in Body Fluids", Journal of Clinical Laboratory Analysis, vol. 7, Issue 6, 1993, pp. 376-393; Cited in the Chinese Office Action dated Apr. 24, 2020 in a counterpart Chinese patent application.

The Chinese Office Action dated Apr. 24, 2020 in a counterpart Chinese patent application No. 201780010831.9.

Harry Levine III, "Alzheimer's β-peptide oligomer formation at physiologic concentrations", Analytical Biochemistry, 2004, pp. 81-90, vol. 335.

(Continued)

*Primary Examiner* — Galina M. Yakovleva
(74) *Attorney, Agent, or Firm* — Sughrue Mion, PLLC (57) ABSTRACT

Provided is a method for detecting a test substance, the method including the steps of: forming an immune complex on a first solid phase by bringing a test substance, a labeled antibody, a capture antibody and the first solid phase into contact with one another; transferring the immune complex onto a second solid phase by breaking the binding between the capture antibody and the first solid phase to liberate the immune complex, and bringing the second solid phase and the immune complex into contact with each other, where the second solid phase is bound to the capture antibody; and detecting the test substance by measuring a label contained in the complex on the second solid phase. The test substance detected by the method is a multimeric antigen, particularly amyloid β or tau protein.

15 Claims, 5 Drawing Sheets

(56) References Cited

OTHER PUBLICATIONS

Mary J. Savage, et al., "A Sensitive Aβ Oligomer Assay Discriminates Alzheimer's and Aged Control Cerebrospinal Fluid", The Journal of Neuroscience, Feb. 19, 2014, pp. 2887-2897, vol. 34, No. 8.

Yuko Horikoshi, et al., "Development of Aβ terminal end-specific antibodies and sensitive ELISA for Aβ variant", Biochemical and Biophysical Research Communications, 2004, pp. 733-737, vol. 319.

Masood Kamali-Moghaddam, et al., "Sensitive detection of Aβ protofibrils by proximity ligation—relevance for Alzheimer's disease", BMC Neuroscience, 2010, pp. 1-7, vol. 11, No. 124.

Lei Wang-Dietrich, et al., "The Amyloid-β Oligomer Count in Cerebrospinal Fluid is a Biomarker for Alzheimer's Disease", Journal of Alzheimer's Disease, 2013, pp. 985-994, vol. 34.

Katja Kuhbach, et al., "Application of an Amyloid Beta Oligomer Standard in the sFIDA Assay", Frontiers in Neuroscience, Technology Report, Jan. 29, 2016, pp. 1-6, vol. 10, Article 8.

International Search Report for PCT/JP2017/004271 dated May 9, 2017 [PCT/ISA/210].

The Communication pursuant to Article 94(3) EPC dated Jan. 22, 2021 in a counterpart European patent application No. 17750220.0.

\* cited by examiner

N.D. = Not Detected

Fig. 9

N.D. = Not Detected

Fig. 10

METHOD FOR DETECTING TEST SUBSTANCE AND REAGENT KIT FOR DETECTING TEST SUBSTANCE

CROSS REFERENCE TO THE RELATED APPLICATION

This application is a continuation application, under 35 U.S.C. § 111(a), of international application No. PCT/JP2017/004271, filed Feb. 6, 2017, which claims priority to Japanese patent application No. 2016-021610, filed Feb. 8, 2016.

TECHNICAL FIELD

The present invention relates to a method for detecting a test substance and a reagent kit for detecting a test substance.

BACKGROUND

A sandwich immunoassay that is widely used as an immunological measurement method is a method in which a labeled antibody and a capture antibody are bound to an antigen in a sample, and the antigen is detected on the basis of a label. In the sandwich immunoassay, two kinds of antibodies with different epitopes are normally used because when an epitope for a labeled antibody and an epitope for a capture antibody overlap one another, only one of the antibodies is bound to an antigen due to steric hindrance, so that detection cannot be performed. However, when the antigen is a multimer, a plurality of identical epitopes are present in the antigen. When two kinds of antibodies with overlapping epitopes are used as a labeled antibody and a capture antibody, a monomer is not detected, and a multimer is detected.

For example, Patent Literature 1 and Non-Patent Literature 1 describe a sandwich immunoassay using a detection antibody and a capture antibody. In these literatures, an epitope of the detection antibody and an epitope of the capture antibody are identical to each other, or overlap one another, so that a multimer of amyloid β can be detected. Non-Patent Literatures 2 to 4 describe a sandwich immunoassay using a detection antibody and two kinds of capture antibodies. In these documents, all of an epitope of the detection antibody and epitopes of the two kinds of capture antibodies are identical to one another, or overlap one another, so that a multimer of amyloid β can be detected.

CITATIONS LIST

Patent Literature

Patent Literature 1: U.S. Patent Application Publication No. 2010/021943

Non-Patent Literatures

Non-Patent Literature 1: Savage, et al., J. Neuroscience 2014, 34(8):2884-97
Non-Patent Literature 2: LeVine III, Anal. Biochem. 335 (2004) 81-90
Non-Patent Literature 3: Kamali-Moghaddam, et al., BMC Neuroscience 2010, 11:124
Non-Patent Literature 4: Wang-Dietrich, et al., J. Alzheimer's Disease 34 (2013)985-94

SUMMARY

The present invention provides a method for detecting a test substance. The method includes the steps of: forming on a first solid phase a complex containing a test substance, a labeled antibody, a first capture antibody and a second capture antibody by bringing the test substance, the labeled antibody, the first capture antibody, the second capture antibody and the first solid phase into contact with one another, where the labeled antibody is bound to the test substance, the first capture antibody is bound to the test substance, the second capture antibody is bound to the test substance, and the first solid phase is bound to the first capture antibody; transferring the complex onto a second solid phase by breaking the binding between the first capture antibody and the first solid phase to liberate the complex, and bringing the second solid phase and the complex into contact with each other, where the second solid phase is bound to the second capture antibody; and detecting the test substance by measuring a label contained in the complex on the second solid phase. In the method, the test substance is a multimer, and an epitope for the labeled antibody, an epitope for the first capture antibody and an epitope for the second capture antibody overlap one another.

The present invention also provides a method for detecting a test substance in a different aspect. The method includes the steps of: forming on a first solid phase a complex containing a test substance, a labeled antibody and a capture antibody by bringing the test substance, the labeled antibody, the capture antibody and the first solid phase into contact with one another, where the labeled antibody is bound to the test substance, the capture antibody is bound to the test substance, and the first solid phase is bound to the capture antibody; transferring the complex onto a second solid phase by breaking the binding between the capture antibody and the first solid phase to liberate the complex, and bringing the second solid phase and the complex into contact with each other, where the second solid phase is bound to the capture antibody; and detecting the test substance by measuring a label contained in the complex on the second solid phase. In the method, the test substance is a multimer, and an epitope for the labeled antibody and an epitope for the capture antibody overlap one another.

The present invention also provides a method for detecting a test substance in a different aspect. The method includes the steps of: forming on a first solid phase a complex containing a test substance, a labeled antibody and a capture antibody by bringing the test substance, the labeled antibody, the capture antibody and the first solid phase into contact with one another, where the labeled antibody is bound to the test substance, the capture antibody is bound to the test substance, and the first solid phase is bound to the capture antibody; breaking the binding between the capture antibody and the first solid phase to liberate the complex on the first solid phase, and transferring the complex to the second solid phase bound to the capture antibody; and detecting the test substance by measuring a label contained in the complex on the second solid phase. In the method, the test substance is amyloid β or tau protein.

BRIEF DESCRIPTION OF DRAWINGS

FIGS. 3(A) to 3(E) show a measurement mechanism in a third embodiment.

DESCRIPTION OF EMBODIMENTS

In a method for detecting a test substance according to one embodiment of the present invention, a test substance is detected by an immune complex transfer method (hereinafter, also referred to as "ICT-EIA") including steps as described below. Hereinafter, embodiments of the present invention will be described.

First Embodiment

In this embodiment, a multimer is detected as a test substance. The "multimer" is also called a polymer, and is formed by physically or chemically polymerizing or aggregating a plurality of monomer molecules. Examples of the monomer molecule include polypeptides, nucleic acids and sugar chains. Specific examples of the polypeptide multimer include amyloid β oligomers obtained by polymerization of amyloid β monomers, and tau oligomers obtained by polymerization of tau proteins. Other examples of the polypeptide multimer include serum-amyloid-A-protein-aggregates, IgG-light chain-aggregates, AapoAI-aggregates, AapoAII-aggregates, ATTR-aggregates, DISC1-aggregates, FUS-aggregates, IAPP-aggregates, SOD1-aggregates, α-synuclein-aggregates, TDP-43-aggregates, huntingtin-aggregates and lysozyme-aggregates. The "multimer" is merely required to include a plurality of monomer molecules, and may include other molecules. In the "multimer", it is not necessarily required that monomer molecules be tightly bonded together by covalent bonding or the like, and the "multimer" also includes aggregates in which monomer molecules are aggregated and gathered by more loose bonding.

The amyloid β is normally a polypeptide including about 40 amino acids, and has the quality of being aggregated to form insoluble amyloid fibrils. The tau protein, which is also called "tau", is a protein having a molecular weight of about 50,000, and has a function of, for example, stabilizing a cytoskeletons by binding to minute microtubules in cells. In a human, the tau protein encompasses six isoforms according to selective splicing of exon 2, exon 3 and exon 10. In this specification, the term "tau protein" or "tau" includes any of the isoforms unless otherwise specified.

The test substance is contained in a sample derived from an organism. Examples of the sample include samples taken from living bodies or dead bodies, and cultured cells. Specific examples of the sample include brain tissues, blood (total blood), plasma, serum and cerebrospinal fluids. The species of the organism is not particularly limited, and the sample can be taken from a human or a non-human mammal.

(Step of Forming Complex)

The detection method according to this embodiment includes the step of forming on a first solid phase a complex containing a test substance, a labeled antibody, a first capture antibody and a second capture antibody by bringing the test substance, the labeled antibody, the first capture antibody, the second capture antibody and the first solid phase into contact with one another, where the labeled antibody is bound to the test substance, the first capture antibody is bound to the test substance, the second capture antibody is bound to the test substance, and the first solid phase is bound to the first capture antibody. In this specification, the "antibody" also includes antigen binding antibody fragments such as Fab and F(ab')$_2$, and derivatives thereof. The formation step is normally carried out in a solution.

In this embodiment, an epitope of the labeled antibody, an epitope of the first capture antibody and an epitope of the second capture antibody overlap one another. The phrase "epitopes overlap one another" means that epitopes for these antibodies are identical or partially identical to one another. When epitopes are identical or partially identical to one another, only one antibody is bound to the epitope of a monomer molecule, and the other antibodies are inhibited from being bound by steric hindrance. By using a plurality of kinds of antibodies with overlapping epitopes in an immunological measurement method, a multimer containing a plurality of epitopes is detected. Particularly, in this embodiment, three kinds of antibodies are used, and therefore detection of a monomer molecule and detection of a multimer (dimer) containing two monomers are suppressed, so that a multimer containing three or more monomers is suitably detected.

The labeled antibody is not particularly limited as long as it is an antibody which can be bound specifically to a test substance, and is labeled with a known labeling substance that is commonly used in an immunological method. Such a labeled antibody can be prepared by binding or linking an antibody and a labeling substance by a known method using a suitable crosslinking agent, a commercially available labeling kit or the like.

The labeling substance is not particularly limited as long as it is a substance capable of emitting a measurable signal, and examples thereof include enzymes, fluorescent substances and radioactive isotopes. Examples of the enzyme include alkaline phosphatase, β-galactosidase, peroxidase, glucose oxidase, tyrosinase, acid phosphatase and luciferase. Examples of the fluorescent substance include fluorescent dyes such as fluorescein isothiocyanate (FITC), and fluorescent proteins such as green fluorescent protein (GFP). Examples of the radioactive isotope include $^{125}$I, $^{14}$C and $^{32}$P. Among them, enzymes are particularly preferable as labeling substances.

The first solid phase can be selected from known solid phases that are commonly used in an immunological method. Examples of the material of the solid phase include latex, rubber, polyethylene, polypropylene, polystyrene, styrene-butadiene copolymers, polyvinyl chloride, polyvinyl acetate, polyacrylamide, polymethacrylate, styrene-methacrylate copolymers, polyglycidyl methacrylate, acrolein-ethylene glycol dimethacrylate copolymers, polyvinylidene difluoride (PVDF), silicone, agarose, gelatin, red blood cells, silica gels, glass, inert alumina and magnetic substances. One of these materials may be used, or two or more of these materials may be combined. As a shape of the solid phase, mention is made of, for example, microtiter plates, test tubes, particles and the like. The particles may be magnetic. Magnetic particles are known in the art, and examples thereof include particles containing $Fe_2O_3$ and/or $Fe_3O_4$, cobalt, nickel, ferrite and magnetite as base materials.

The first capture antibody in the complex is bound to the first solid phase to immobilize the complex on the first solid phase. The mode of binding of the first capture antibody to the first solid phase is not particularly limited as long as the binding can be broken, and examples thereof include physical adsorption and ionic bonding. The first capture antibody and the first solid phase can also be bound to each other using a substance that is interposed between the first capture antibody and the first solid phase. Such a substance is preferably a combination of two substances that can be bound specifically to each other, and dissociated (these two substances are referred to as a "binding substance" and a "binding partner", respectively). For example, by binding a binding substance to the first capture antibody, and binding a binding partner to the first solid phase, the first capture antibody and the first solid phase can be bound to each other by means of affinity between the binding substance and the binding partner. Combinations of a binding substance and a binding partner are known in the art, and examples thereof include combinations of an antigen (excluding a test substance) and its associated antibody, a ligand and its associated receptor, an oligonucleotide and its associated complementary strand, a biotin (such as biotin, or a biotin analogue such as desthiobiotin), an avidin (such as avidin, or an avidin analogue such as streptavidin), nickel and a histidine tag, and glutathione and glutathione-S-transferase. As combinations of an antigen and an antibody, combinations of a hapten and an anti-hapten antibody, and a biotin (or desthiobiotin) and an anti-biotin antibody (or anti-desthiobiotin antibody) are preferable. As a combination of a hapten and an anti-hapten antibody, a combination of 2,4-dinitrophenol (DNP) and an anti-DNP antibody is particularly preferable.

Which is used as a binding substance and which is used as a binding partner in the above-mentioned combination is not particularly limited. For example, in the case of a combination of a hapten and an anti-hapten antibody, an anti-hapten antibody may be used as a binding partner with a hapten used as a binding substance, or a hapten may be used as a binding partner with an anti-hapten antibody used as a binding substance. Since the binding substance is bound to the first capture antibody, it is preferable to use an anti-hapten antibody as a binding partner with a hapten used as a binding substance. A method for binding a binding substance or binding partner to an antibody and a first solid phase is known in the art. For example, when a first capture antibody and a biotin is bound to each other, a method using a crosslinking agent (e.g. maleimide, N-hydroxysuccinimide or the like) that reacts with an amino group or a thiol group in the antibody is known. As a method for binding a binding partner and a first solid phase to each other, a physical adsorption method, a covalent bonding method, an ionic bonding method or the like is known.

In the formation step, a test substance, the labeled antibody, the first capture antibody and the second capture antibody are bound to one another through an antigen-antibody reaction to form a sandwich complex containing a "labeled antibody-test substance-first capture antibody and second capture antibody". The first capture antibody contained in the complex is captured by the first solid phase.

The addition amount of the labeled antibody, the first capture antibody, the second capture antibody and the first solid phase is not particularly limited, but they are added normally in excess of the predicted amount of a test substance. The order of bringing the labeled antibody, the first capture antibody, the second capture antibody, the first solid phase and a test substance-containing sample into contact with one another is not particularly limited. Preferably, the labeled antibody, the first capture antibody, the second capture antibody and the test substance are brought into contact with one another to form a complex, followed by bringing the first solid phase into contact with the complex. Alternatively, the first capture antibody and the first solid phase are first brought into contact with each other.

The reaction temperature and the reaction time in the formation step are not particularly limited, and normally the labeled antibody, the first capture antibody, the second capture antibody, the first solid phase and the test substance may be left standing at a temperature of 20 to 45° C. for 15 to 30 minutes, or gently stirred.

It is preferable to carry out a step of recovering the first solid phase after the formation step. In the reaction system, unreacted components such as constituent components of the pretreatment liquid, impurities contained in the sample, and excess antibodies and the like remain in addition to the first solid phase on which the complex is formed. Here, the "unreacted component" means a component other than the complex bound on the first solid phase, which is a free component that is not bound to the first solid phase. For example, a complex containing only a labeled antibody and a first capture antibody is an unreacted component. The recovery step is generally called B/F separation, and the first solid phase is separated from unreacted components, and recovered. Therefore, unreacted components which adversely affect a measurement step as described later can be removed through the recovery step. In the recovery step, it is not necessary to completely remove unreacted components, and may remain as long as measurement is not adversely affected.

A method for recovering the first solid phase in the sample is itself known in the art, and can be appropriately determined according to the kind of the first solid phase. For example, when magnetic particles are used, the first solid phase in the sample can be recovered by magnetic separation. Specifically, a magnet is brought close to the wall surface of a container containing the sample obtained in the formation step, so that magnetic particles in the sample are fixed to the wall surface of the container, and the liquid phase is suctioned and removed to recover the magnetic particles. When gelatin particles or latex particles are used, the particles can be recovered by suctioning and removing the liquid phase after precipitating the particles by centrifugation.

The recovery step may further include a step of washing the recovered first solid phase. Washing of the first solid phase can be performed by, for example, adding a washing liquid to the recovered first solid phase, and then removing the washing liquid from the first solid phase. The washing liquid is preferably a buffer solution which does not impair the complex formed on the first solid phase. Such a washing liquid is particularly preferably a buffer solution containing a surfactant, and examples thereof include TBS-T (Tris buffered saline containing 0.05% Tween 20) and PBST (phosphate buffered saline containing 0.05% Tween 20). A commercially available washing liquid such as a HISCL washing liquid (manufactured by Sysmex Corporation) can also be used. Through the washing step, components that are adsorbed nonspecifically to the first solid phase or the complex can be removed.

(Transfer Step)

Next, a step of liberating the complex on the first solid phase, and transferring the complex to a second solid phase different from the first solid phase is carried out. The liberation is normally performed in a solution. Here, a method for liberating the complex on the solid phase is itself known in the art. Mention is made of, for example, a method using a substance capable of breaking binding between the first capture antibody in the complex obtained in the formation step and the first solid phase (hereinafter, referred to as a "releasing agent"). A releasing agent is known in the art, and can be appropriately selected according to the mode of binding of the first capture antibody and the first solid phase.

For example, when the first capture antibody in the complex and the first solid phase are bound to each other by physical adsorption, the complex can be liberated by using as the releasing agent a solution containing a surfactant. In the case of ionic bonding, the complex can be liberated by using a solution containing ions.

When the first capture antibody and the first solid phase are bound to each other by means of affinity between a binding substance and a binding partner, the complex can be liberated by using a releasing agent that breaks the binding between the binding substance and the binding partner. Such a releasing agent is also known in the art, and can be appropriately selected according to the combination of a binding substance and a binding partner. For example, in the case of binding of a hapten and an anti-hapten antibody, the hapten or a derivative thereof can be used as a releasing agent. In the case of binding of a biotin (or desthiobiotin) and an avidin (or streptavidin), a biotin can be used as a releasing agent.

In the case of liberating the complex using a releasing agent, the treatment temperature and treatment time can be appropriately set according to the kind of releasing agent. Normally, the complex and the first solid phase may be left standing at a temperature of 20 to 45° C. for 3 to 8 minutes, or gently stirred.

In the transfer step, the complex liberated from the first solid phase in the manner described above is transferred to a second solid phase by bringing the complex into contact with the second solid phase different from the first solid phase, and binding the complex to the second solid phase. Here, in this specification, the "second solid phase different from the first solid phase" means a second solid phase different from the first solid phase which has been present since addition of the first solid phase in the formation step (hereinafter, also referred to simply as a "second solid phase"). That is, in this transfer step, the liberated complex is not intended to be bound again with the first solid phase which has been present since addition of the first solid phase in the formation step. In this embodiment, the complex liberated from the first solid phase is recovered, and brought into contact with the newly provided second solid phase. For example, when particles are used as the first solid phase, the complex is liberated from the first solid phase, the first solid phase is immobilized on the wall surface or the bottom portion of a container by a magnetic force, centrifugal separation or the like in the same manner as in the recovery step. The liquid phase containing the complex can be recovered, and brought into contact with the second solid phase. The complex and the second solid phase are brought into contact with each other normally in a solution. The material and the shape of the second solid phase are the same as in the first solid phase described above. The material and the shape of the second solid phase may be different from or identical to the material and the shape of the first solid phase.

In this embodiment, the second capture antibody contained in the liberated complex is bound to the second solid phase to immobilize the complex on the second solid phase. The mode of binding of the second solid phase and the complex is not particularly limited, but it is preferable to bind the second solid phase and the complex to each other using a substance interposed between the second capture antibody in the complex and the second solid phase. Examples of the substance include the above-mentioned combinations of a binding substance and a binding partner. For example, by binding the binding substance to the second capture antibody beforehand as a "binding site to the second solid phase", and binding the binding partner to the second solid phase, the second capture antibody in the complex and the second solid phase can be bound to each other by means of affinity between the binding substance and the binding partner. The combination of a binding substance and a binding partner is preferably a combination of a biotin and an avidin. The combination of a binding substance and a binding partner for binding the second capture antibody and the second solid phase to each other is preferably different from the combination of a binding substance and a binding partner for binding the first capture antibody and the first solid phase to each other. For example, a first capture antibody to which DNP is bound, a first solid phase on which an anti-DNP antibody is immobilized, a second capture antibody to which a biotin is bound, and a second solid phase on which streptavidin is immobilized can be used.

The treatment temperature and the treatment time for transferring the complex to the second solid phase are not particularly limited, and normally, the complex and the solid phases may be left standing at a temperature of 20 to 45° C. for 1 to 30 minutes, or gently stirred. Particularly, when the second solid phase is in the shape of particles, the complex and the solid phases may be left standing for 1 to 5 minutes, or gently stirred.

It is preferable to carry out a step of recovering the second solid phase after the transfer step and before the measurement step. The step of recovering the second solid phase can be carried out by the same method as in the step of recovering the first solid phase.

(Measurement Step)

In the measurement step, a label contained in the complex on the second solid phase is measured. Here, a method for measuring the label is itself known in the art. In the embodiment of the present invention, it is possible to select an appropriate measurement method according to the kind of signal derived from the above-mentioned labeling substance. For example, when the labeling substance is an enzyme, a signal such as light or a color generated by reacting a substrate for the enzyme using a known apparatus. Examples of the measurement apparatus include spectrophotometers and luminometers.

The substrate of the enzyme can be appropriately selected from known substrates according to the kind of enzyme. For example, when an alkaline phosphatase is used as an enzyme, examples of the substrate include chemiluminescent substrates such as CDP-Star (registered trademark) (disodium 4-chloro-3-(methoxyspiro[1,2-dioxetane-3,2'-(5'-chloro)tricyclo[3.3.1.1$^{3,7}$]decane]-4-yl) phenylphosphate) and CSPD (registered trademark) (disodium 3-(4-methoxyspiro[1,2-dioxetane-3,2-5'-chloro)tricyclo[3.3.1.1$^{3,7}$]decane]-4-yl)phenyl phosphate); luminescent substrates such as p-nitrophenyl phosphate, 5-bromo-4-chloro-3-indolylphosphoric acid (BCIP), 4-nitrobluetetrazolium chloride (NBT) and iodonitrotetrazolium (INT); fluorescent substrates such as 4-methylumbelliphenyl phosphate (4MUP); and chromogenic substrates such as 5-bromo-4-chloro-3-indolylphosphoric acid (BCIP), disodium 5-bromo-6-chloro-indolylphosphate and p-nitrophenyl phosphorus. When β-galactosidase is used as an enzyme, examples of the substrate include 4-methylumbelliferyl-β-D-galactopyranoside.

When the labeling substance is a radioactive isotope, a radiation as a signal can be measured using a known apparatus such as a scintillation counter. When the labeling substance is a fluorescent substance, fluorescence as a signal can be measured using a known apparatus such as a fluorescence microplate reader.

On the basis of results of the measurement described above, a test substance is detected. Here, the term "detect" includes qualitative detection, quantification and semi-quantification as to whether a test substance is present or absent. The term "semi-quantify" means that the content of a test substance is determined in the grade of being "negative", "weakly positive", "strongly positive" or the like.

When a test substance is qualitatively detected, it is preferable that a threshold with which negative samples and positive samples can be accurately classified, and a measurement result is compared with the threshold to determine whether the test substance is present or absent. For the threshold, the test substance concentration is measured beforehand using a plurality of samples that do not contain a test substance or contain the test substance in a very small amount (e.g. biological samples obtained from healthy subjects) and a plurality of samples containing the test substance (e.g. biological samples obtained from patients with a nervous system disease such as Alzheimer dementia). A value with which negative groups and positive groups can be most accurately classified can be used as the threshold. A person skilled in the art can appropriately set the threshold according to the purpose of measurement in consideration of a sensitivity, a specificity, a positive predictive value, a negative predictive value and the like.

A specific example of a measurement mechanism in this embodiment will be described with reference to FIGS. 1(A) to 1(E). This specific example shows a system that suitably detects a trimeric or higher-order oligomer of amyloid β (shown as Aβ in the drawing). This is merely an example, and does not limit the present invention.

Figure 1A:
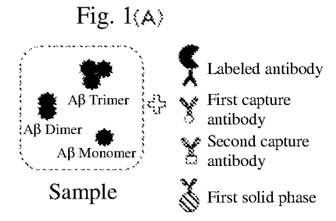
FIGS. 1(A) to 1(E) show a measurement mechanism in a first embodiment.
Figure 1B:
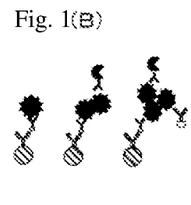
Figure 1C:
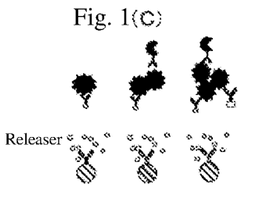
Figure 1D:
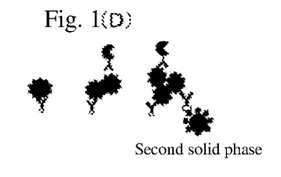
Figure 1E:
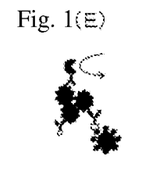

FIG. 1(A): A sample containing a monomer, a dimer and a trimer of amyloid β is mixed with a labeled antibody, a first capture antibody, a second capture antibody and a first solid phase. The labeled antibody is labeled with an enzyme. DNP is added to the first capture antibody. A biotin is added to the second capture antibody. The first solid phase is in the form of particles on which an anti-DNP antibody is immobilized. The labeled antibody, the first capture antibody and the second capture antibody are identical monoclonal antibodies that recognize a specific epitope of amyloid β. In other words, the epitopes for these antibodies are identical to each other. FIG. 1(B): The first capture antibody is bound to the monomer. The first capture antibody and the labeled antibody are bound to the dimer. The first capture antibody, the second capture antibody and the labeled antibody are bound to the trimer. FIG. 1(C): After B/F separation, DNP-Lys (DNP-lysine) is added as a releasing agent to liberate a complex of amyloid β and antibody from the first solid phase. FIG. 1(D): A second solid phase with streptavidin immobilized thereon is added to a liquid phase fraction containing the complex obtained in the step (C). Accordingly, the complex containing amyloid β trimer is bound to the second solid phase. FIG. 1(E): After B/F separation, an enzyme substrate is added, and luminescence generated by an enzyme reaction is measured.

The first capture antibody is bound to the monomer in the example in FIG. 1(B), but there may be a monomer to which the labeled antibody or the second capture antibody, rather than the first capture antibody, is bound. When the labeled antibody or the second capture antibody is bound, a signal is not detected from this complex. The first capture antibody and the labeled antibody are bound to the dimer in this example, but two molecules of the same kind or different kinds of antibodies, among the first capture antibody, the second capture antibody and the labeled antibody, may be bound to the dimer. In any case, a signal is not detected from this complex. The first capture antibody, the second capture antibody and the labeled antibody are bound to the trimer in this example, but the same kind of antibodies may be bound to at least two of the three epitopes. In this case, a signal is not detected from this complex.

As described above, only a complex to which one or more molecule of each of all the first capture antibody, the second capture antibody and the labeled antibody is bound is subjected to solid phase transfer or enzymatic reaction to generate a signal. The higher the degree of polymerization of the test substance, the higher the probability that one or more molecules of each of the first capture antibody, the second capture antibody and the labeled antibody are bound to the test substance. On the other hand, the lower the degree of polymerization of the test substance, the higher the probability that even one molecule of each of all the kinds of antibodies is not bound to the test substance. With the method of this embodiment, a signal from a low-molecular-weight oligomer is suppressed, so that a high-molecular-weight oligomer can be detected more accurately.

Second Embodiment

In this embodiment, a multimer is detected as a test substance. The "multimer" and the "sample" containing a test substance are the same as described in the first embodiment.

(Step of Forming Complex)

The detection method according to this embodiment includes the step of forming on a first solid phase a complex containing a test substance, a labeled antibody and a capture antibody by bringing the test substance, the labeled antibody, the capture antibody and the first solid phase into contact with one another, where the labeled antibody is bound to the test substance, the capture antibody is bound to the test substance, and the first solid phase is bound to the capture antibody. The "antibody" is the same as described in the first embodiment.

In this embodiment, an epitope for the labeled antibody and an epitope for the capture antibody overlap one another. The phrase "epitope overlaps one another" is the same as described in the first embodiment. In this embodiment, two kinds of antibodies are used, and therefore detection of a monomer molecule is suppressed, so that a multimer is suitably detected.

The labeled antibody is the same as described in the first embodiment.

The first solid phase is the same as described in the first embodiment.

In this embodiment, a first binding substance and a second binding substance are bound to the capture antibody, and a first binding partner that is bound specifically to the first binding substance is immobilized on the first solid phase, and a second binding partner that is bound specifically to the second binding substance is immobilized on the second solid phase. The mode of binding of the capture antibody and the first solid phase is the same as the mode of binding of the first capture antibody and the first solid phase which has been described in the first embodiment. The mode of binding of the capture antibody and the second solid phase is the same as the mode of binding of the first capture antibody and the second solid phase which has been described in the first embodiment.

In the formation step, a test substance, the labeled antibody and the capture antibody are bound to one another through an antigen-antibody reaction to form a sandwich complex containing a "labeled antibody-test substance-capture antibody". The capture antibody contained in the complex is captured by the first solid phase.

The addition amount of the labeled antibody, the capture antibody and the first solid phase is the same as described in the first embodiment. The order of bringing the labeled antibody, the capture antibody, the first solid phase and a test substance-containing sample into contact with one another is the same as described above.

It is preferable to carry out a step of recovering the first solid phase after the formation step. The recovery step is the same as described in the first embodiment.

(Transfer Step)

Liberation of the complex from the first solid phase is the same as described in the first embodiment.

In this embodiment, unlike the first embodiment, the capture antibody includes both the first binding substance and the second binding substance. The second binding substance of the capture antibody contained in the liberated complex and the second binding partner on the second solid phase are bound to each other to immobilize the liberated complex on the second solid phase.

It is preferable to carry out a step of recovering the second solid phase after the transfer step and before the measurement step. The step of recovering the second solid phase can be carried out by the same method as in the step of recovering the first solid phase.

(Measurement Step)

Measurement of the label and detection of the test substance are the same as described in the first embodiment.

A specific example of a measurement mechanism in this embodiment will be described with reference to FIGS. 2(A) to 2(E). This specific example shows a system that detects a dimeric or higher-order oligomer of amyloid β (shown as Aβ in the drawing). This is merely an example, and does not limit the present invention.

Figure 2A:
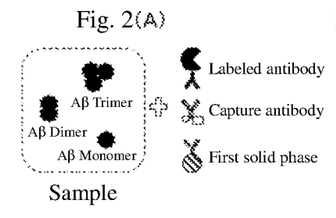
FIGS. 2(A) to 2(E) show a measurement mechanism in a second embodiment.

FIG. 2(A): A sample containing a monomer, a dimer and a trimer of amyloid β is mixed with a labeled antibody, a capture antibody and a first solid phase. The labeled antibody is labeled with an enzyme. DNP (indicated by circles in the drawing) and a biotin (indicated by squares in the drawing) are added to the capture antibody. The first solid phase is in the form of particles on which an anti-DNP antibody is immobilized. The labeled antibody and the capture antibody are identical monoclonal antibodies that recognize a specific epitope of amyloid β. In other words, the epitopes for these antibodies are identical to each other.

Figure 2B:
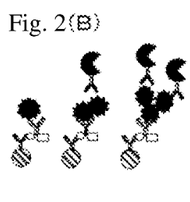

FIG. 2(B): The capture antibody is bound to the monomer. The capture antibody and the labeled antibody are bound to the dimer. The capture antibody and two molecules of the labeled antibody are bound to the trimer.

Figure 2C:
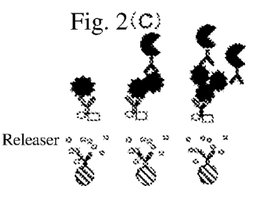

FIG. 2(C): After B/F separation, DNP-Lys (DNP-lysine) is added as a releasing agent to liberate the complex of amyloid β and the antibody from the first solid phase.

Figure 2D:
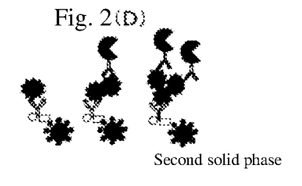

FIG. 2(D): A second solid phase with streptavidin immobilized thereon is added to a liquid phase fraction containing the complex obtained in the step (C). Accordingly, the complex and the second solid phase are bound to each other.

Figure 2E:
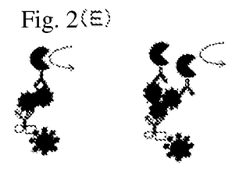

FIG. 2(E): After B/F separation, an enzyme substrate is added, and luminescence generated by an enzyme reaction is measured.

The capture antibody is bound to the monomer in the example in FIG. 2(B), but there may be a monomer to which the labeled antibody, rather than the capture antibody, is bound. When the labeled antibody is bound, a signal is not detected from this complex.

The capture antibody and the labeled antibody are bound to the dimer in this example, but two molecules of the same or different kinds of antibodies, among the capture antibody and the labeled antibody, may be bound to the dimer. When two molecules of the capture antibody or two molecules of the labeled antibody are bound to the dimer, a signal is not detected.

In this example, the capture antibody and two molecules of the labeled antibody are bound to the trimer, and when three molecules of the capture antibody or three molecules of the labeled antibody are bound to the trimer, a signal is not detected.

As described above, only a complex to which one or more molecule of each of both the capture antibody and the labeled antibody is bound is subjected to solid phase transfer or enzymatic reaction to generate a signal. One or more molecule of each of the capture antibody and the labeled antibody is likely bound to a test substance having a high degree of polymerization. On the other hand, the lower the degree of polymerization of the test substance, the higher the probability that even one molecule of each of all the kinds of antibodies is not bound to the test substance. With the method of this embodiment, a signal from a low-molecular-weight oligomer is suppressed, so that a high-molecular-weight oligomer can be detected more accurately.

Third Embodiment

In this embodiment, amyloid β and tau protein are detected as test substances. In this embodiment, an epitope for the labeled antibody and an epitope for the capture antibody are different from each other, and the labeled antibody and the capture antibody may be bound to different sites of amyloid β or tau protein as a test substance in this embodiment. Accordingly, not only a multimer but also a monomer molecule can be detected. In other respects, the third embodiment is the same as the second embodiment.

A specific example of a measurement mechanism in this embodiment will be described with reference to FIGS. 3(A) to 3(E). This specific example shows a system that detects amyloid β (shown as Aβ in the drawing). This is merely an example, and does not limit the present invention.

Figure 3A:
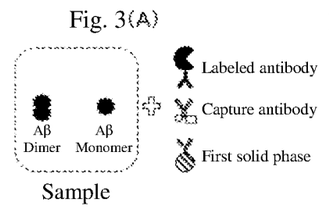

FIG. 3(A): A sample containing a monomer and a dimer of amyloid β is mixed with a labeled antibody, a capture antibody and a first solid phase. The labeled antibody is labeled with an enzyme. DNP (indicated by circles in the drawing) and a biotin (indicated by squares in the drawing) are added to the capture antibody. The first solid phase is in the form of particles on which an anti-DNP antibody is immobilized. The labeled antibody and the capture antibody are different in epitope, and are bound at different positions in the amino acid sequence of amyloid β.

Figure 3B:
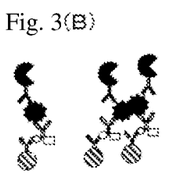

FIG. 3(B): The capture antibody and the labeled antibody are bound to the monomer and the dimer, respectively.

Figure 3C:
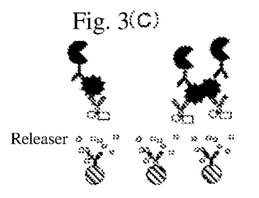

FIG. 3(C): After separation of B/F, DNP-Lys (DNP-lysine) is added as a releasing agent to liberate the complex from the first solid phase.

Figure 3D:
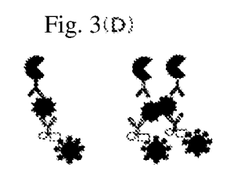

FIG. 3(D): A second solid phase with streptavidin immobilized thereon is added to a liquid phase fraction containing the complex obtained in the step (C). Accordingly, the complex and the second solid phase are bound to each other.

FIG. 3(E): After B/F separation, an enzyme substrate is added, and luminescence generated by an enzyme reaction is measured.

The sample includes a monomer and a dimer in the example in FIG. 3(A), but the capture antibody and the labeled antibody can also be bound to a trimeric or higher-order multimer to detect a signal.

As described above, only a complex to which one or more molecule of each of both the capture antibody and the labeled antibody is bound is subjected to solid phase transfer or enzymatic reaction to generate a signal. One or more molecule of each of the capture antibody and the labeled antibody is likely bound to a test substance having a high degree of polymerization. On the other hand, the lower the degree of polymerization of the test substance, the higher the probability that even one molecule of each of all the kinds of antibodies is not bound to the test substance. With the method of this embodiment, a signal from a low-molecular-weight oligomer is suppressed, so that a high-molecular-weight oligomer can be detected more accurately.

(Reagent Kit Used in First Embodiment)

A reagent kit includes a labeled antibody, a first capture antibody and a second capture antibody. The reagent kit may further include a first solid phase and a second solid phase. When the label is an enzyme, the reagent kit may further include a substrate of the enzyme. The reagent kit may further include a releasing agent for separating a complex from the first solid phase. Some of these reagents may be contained in one container, but each reagent may be contained in a separate container for suppressing a nonspecific reaction in the container. When the label is an enzyme, the labeled antibody and the substrate required to be contained in separate containers. Since the releasing agent is added to the reaction system after formation of the complex on the first solid phase, it is preferable that the releasing agent is contained in a container different from containers for other reagents. These reagents are provided to a user in a dry state or in a liquid form (in a state of being dissolved or dispersed in a liquid), but these reagents are preferably in a liquid form because it is preferable that a chemical reaction in the above-mentioned detection method is carried out in a solution. Details of these reagents are the same as described in the first embodiment.

The reagent kit may further include other reagents. For example, the reagent kit includes a buffer solution. The buffer solution is not particularly limited as long as it is a buffer solution having a buffering action at a pH of 6.5 to 8, and examples thereof include phosphate buffer solutions (PBS), imidazole buffer solutions, triethanolamine hydrochloride buffer solutions (TEA) and Good's buffer solutions. Examples of the Good's buffer solution include buffers such as MES, Bis-Tris, ADA, PIPES, Bis-Tris-Propane, ACES, MOPS, MOPSO, BES, TES, HEPES, HEPPS, Tricine, Tris, Bicine and TAPS. The buffer solution may contain known additives such as a protein stabilizer (BSA or the like), a preservative (sodium azide, phenyl methanesulfonyl fluoride or the like) and an inorganic salt (magnesium chloride, zinc chloride or the like).

Figure 4:
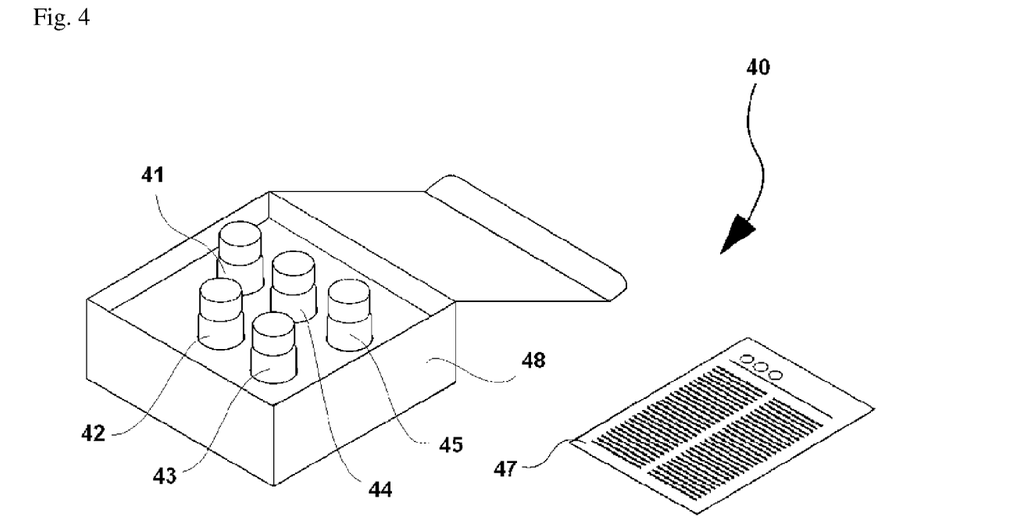
FIG. 4 shows one example of a reagent kit.

An example of a reagent kit is shown in FIG. 4. The reagent kit 40 according to this embodiment includes a first container 41 containing a first capture antibody, a second container 42 containing a second capture antibody, a third container 43 containing particles as a first solid phase, a fourth container 44 containing particles as a second solid phase, and a fifth container 45 containing a labeled antibody. These containers are contained in a packing box 48 together with an attached document 47.

The present invention includes uses of the labeled antibody, the first capture antibody and the second capture antibody for producing a reagent kit to be used in the detection method according to the first embodiment.

(Reagent Kit Used in Second Embodiment)

A reagent kit includes a labeled antibody and a capture antibody. The reagent kit may include only one kind of capture antibody unlike the reagent kit used in the first embodiment. For other configurations, the reagent kit according to this embodiment is the same as described for the reagent kit used in the first embodiment.

Figure 5:
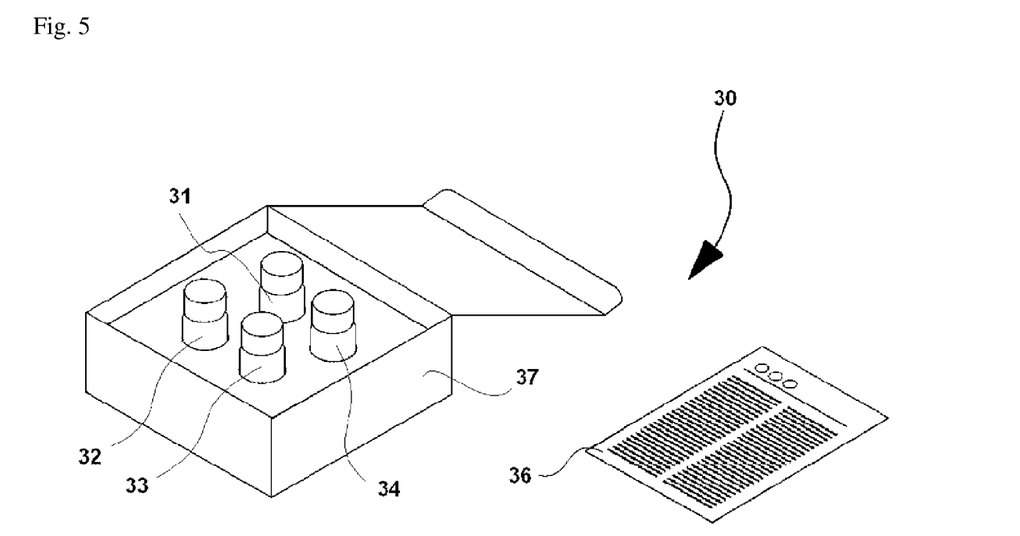
FIG. 5 shows one example of a reagent kit.

An example of a reagent kit is shown in FIG. 5. The reagent kit 30 according to this embodiment includes a first container 31 containing a capture antibody, a second container 32 containing particles as a first solid phase, a third container 33 containing particles as a second solid phase, and a fourth container 34 containing a labeled antibody. These containers are stored in a packing box 38 together with an attached document 37.

The present invention includes uses of the labeled antibody and the capture antibody for producing a reagent kit to be used in the detection method according to the second embodiment.

(Reagent Kit Used in Third Embodiment)

The configuration of a reagent kit is basically the same as that of the reagent kit used in the second embodiment. Epitopes for a capture antibody and a labeled antibody contained in this reagent kit are different from each other.

The present invention includes uses of the labeled antibody and the capture antibody for producing a reagent kit to be used in the detection method according to the third embodiment.

Hereinafter, the present invention will be described in more detail by way of examples, but the present invention is not limited to these examples. In examples, the "particle size" is a diameter.

EXAMPLES

The meaning of each abbreviation hereinafter is as follows.

BSA: bovine serum albumin
DNP: 2,4-dinitrophenyl group
Bio: biothinyl group
OPDM: N,N'-(1,2-phenylene)dimaleimide
SATA: N-succinimide S-acetylthioacetate
EMCS: N-(6-maleimidocaproyloxy)succinimide
SH: thiol group
mal: maleimide group
BSA-Bio-DNP: BSA modified with a biotin and DNP
$(PEG)_8$-BSA-Bio-DNP: BSA-Bio-DNP with PEG linker
4-MUG: 4-methylumbelliferyl-$\beta$-D-galactopyranoside
DMF: N,N-dimethylformamide
PEG: polyethylene glycol chain
(PEG)n: polyethylene glycol chain in which the addition molar number of oxyethylene groups is n
Gal: $\beta$-galactosidase
ALP: alkali phosphatase (Example 1) Detection of Amyloid $\beta$42 by ICT-EIA 1. Preparation of Test Substance Solution A standard substance of amyloid $\beta$42 ELISA Kit (manufactured by Covance Inc., trade name: BetaMark) was diluted with a buffer solution A (containing 0.4 M sodium chloride, 0.1% by mass of BSA and a 0.1 M sodium phosphate buffer solution (pH: 7.0)) in stages to prepare 100 µL of a test substance solution containing 0 pg, 0.003 pg, 0.01 pg, 0.1 pg, 0.3 pg, 1 pg, 3 pg or 10 pg of amyloid $\beta$42.

2. Preparation of Antibody Solution

An antibody labeled with Gal was prepared in the following manner. By a common method, an anti-amyloid $\beta$42 rabbit monoclonal antibody (IgG) (manufactured by Life Technologies Inc., clone name: H31L21) was fragmented with pepsin to obtain a F(ab')$_2$ fragment. The F(ab')$_2$ fragment was reduced to obtain Fab'-SH. Gal was reacted with OPDM to obtain Gal-mal. Fab'-SH was reacted with Gal-mal to obtain a labeled antibody solution containing Fab'-Gal.

A capture antibody with a biotin and DNP bound thereto was prepared in the following manner. By a common method, an anti-amyloid β42 mouse monoclonal antibody (IgG) (manufactured by Covance Inc., clone name: 6E10) was fragmented with pepsin to obtain a F(ab')$_2$ fragment. The obtained F(ab')$_2$ fragment was reduced to obtain Fab'-SH. BSA-Bio-DNP was reacted with a linker (manufactured by Life Technologies Inc., trade name: SM(PEG)8) to obtain BSA-Bio-DNP-(PEG)$_8$-mal. Fab'-SH was reacted with BSA-Bio-DNP-(PEG)$_8$-mal to obtain a capture antibody containing Fab'-(PEG)$_8$-BSA-Bio-DNP.

The labeled antibody solution, the capture antibody solution and the buffer solution A were mixed so as to have a labeled antibody content of 10 fmol and a capture antibody content of 100 fmol, thereby preparing 100 μL of an antibody solution.

3. Preparation of Solid Phase

By a common method, an anti-DNP antibody (rabbit polyclonal antibody prepared by a common method) was immobilized on polystyrene beads (manufactured by ImmunoChemical, Inc., trade name: Immuno bead 6.35 φ) with a particle size of 6.35 mm to prepare an anti-DNP antibody solid phase.

By a common method, streptavidin (manufactured by Wako Pure Chemical Industries, Ltd., trade name: Streptavidin) was immobilized on polystyrene beads (manufactured by ImmunoChemical, Inc., trade name: Immuno bead 6.35 φ) with a particle size of 6.35 mm to prepare a streptavidin solid phase (hereinafter, referred to as a "STA solid phase").

4. Measurement (1) Formation of Complex

100 μL of the measurement sample was mixed with 100 μL of the antibody solution. Incubation was performed at 4° C. for 12 hours to form a sandwich complex of labeled antibody-test substance-capture antibody.

(2) Immobilization of Complex on First Solid Phase

One anti-DNP antibody solid phase was added to 200 μL of a solution containing the complex. Incubation was performed at 25° C. for 30 minutes to immobilize the complex on the solid phase.

The liquid phase was removed, and the complex was washed twice with 2 mL of a washing liquid 1 (containing 0.1 M sodium chloride, 0.1% by mass of BSA and 0.1 M sodium phosphate buffer solution (pH: 7.0)).

(3) Liberation of Complex

150 μL of an eluate 1 (containing 12 mM DNP) was added to the solid phase with the complex immobilized thereon. By performing incubation at 25° C. for 30 minutes, the binding between the anti-DNP antibody solid phase and the complex was broken to liberate the complex.

(4) Immobilization of Complex on Second Solid Phase

The supernatant containing the complex was recovered, and one STA solid phase was added thereto. Incubation was performed at 25° C. for 30 minutes to immobilize the complex on the solid phase. The liquid phase was removed, and the complex was washed with 2 mL of a washing liquid B (containing 0.1 M sodium chloride, 0.1% by mass of BSA and 0.1 M sodium phosphate buffer solution (pH: 7.0)) three times.

(5) Enzyme Reaction and Fluorescence Measurement

200 μL of the buffer solution B and a substrate solution (containing 0.2 mM of 4-MUG) were added to the solid phase with the complex immobilized thereon, and incubation was performed at 30° C. for 20 hours. The reaction liquid was irradiated with excitation light having a wavelength of 360 nm, and the intensity of fluorescence with a wavelength of 450 nm was measured. The fluorescence intensity of a solution which did not contain the solid phase with the complex immobilized thereon, and was obtained by mixing 200 μL of the buffer solution B and the substrate solution was measured in the same manner as described above, and was used as a background value. The background value was subtracted from the fluorescence intensity measured using the solid phase with the complex immobilized thereon.

(Comparative Example 1) Detection of Amyloid β42 by Sandwich ELISA

As a comparison, measurement of amyloid β42 was performed by sandwich ELISA which did not involve transfer of a complex. In the same manner as in Example 1(1) and (2), a complex was immobilized on an anti-DNP antibody solid phase, and washed, and in the same manner as in Example 1(5), a substrate solution was added thereto, incubation was performed at 30° C. for 2 hours, and the fluorescence intensity was measured. In Comparative Example 1, the steps in Example 1(3) and (4) were not carried out.

Results in Example 1 and Comparative Example 1

Figure 6:
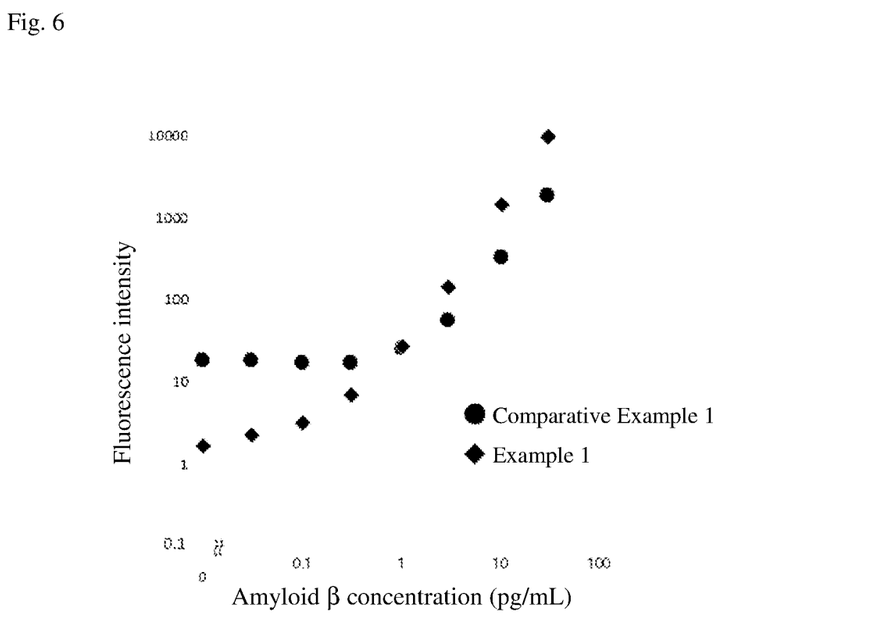
FIG. 6 is a graph showing results in Example 1 and Comparative Example 1.

FIG. 6 shows the fluorescence intensity calculated in each of Example 1 and Comparative Example 1. The detection limit of the method in Example 1 was about 0.1 pg/mL, and the detection limit of the method in Comparative Example 1 was about 1 pg/mL. Thus, the method in Example 1 made it possible to perform detection with a sensitivity higher by a factor of about 10 than that in Comparative Example 1.

(Example 2) Detection of Tau Protein by ICT-EIA

1. Preparation of Test Substance Solution

A tau protein (manufactured by Millipore Corporation, trade name: HUMAN TAU-381) was diluted with a buffer solution A in stages to prepare 70 μL of a test substance solution in such a manner that the concentration of the tau protein was 0 pg/mL, 0.3 pg/mL, 0.6 pg/mL, 1.25 pg/mL, 2.5 pg/mL, 5 pg/mL, 10 pg/mL, 100 pg/mL or 1000 pg/mL.

2. Preparation of Antibody Solution

An antibody labeled with ALP was prepared in the following manner. By a common method, an anti-tau mouse monoclonal antibody (IgG) (manufactured by BioLegend, clone name: TAU12) was fragmented with pepsin to obtain a F(ab')$_2$ fragment. The obtained F(ab')$_2$ fragment was reduced to obtain Fab'-SH. ALP was reacted with EMCS to obtain ALP-mal. Fab'-SH was reacted with ALP-mal to obtain a labeled antibody solution containing Fab'-ALP. The concentration of the labeled antibody was adjusted to 50 fmol/20 μL.

A capture antibody with a biotin and DNP bound thereto was prepared in the following manner. By a common method, an anti-tau mouse monoclonal antibody (IgG) (manufactured by Covance Inc., clone name: TAU5) was fragmented with pepsin to obtain a F(ab')$_2$ fragment. The obtained F(ab')$_2$ fragment was reduced to obtain Fab'-SH.

BSA-Bio-DNP was reacted with a linker (manufactured by Life Technologies Inc., trade name: SM(PEG)8) to obtain BSA-Bio-DNP-(PEG)$_8$-mal. Fab'-SH was reacted with BSA-Bio-DNP-(PEG)$_8$-mal to obtain a capture antibody containing Fab'-(PEG)$_8$-BSA-Bio-DNP. The concentration of the capture antibody was adjusted to 200 fmol/20 µl.

3. Preparation of Solid Phase

By a common method, an anti-DNP antibody (manufactured by Sysmex Corporation) was immobilized on magnetic particles with a particle size of 2.2 µm (manufactured by JSR Corporation, trade name: MAG 2201) to prepare an anti-DNP antibody solid phase.

As a streptavidin solid phase (hereinafter, referred to as a "STA solid phase"), a HISCL R2 reagent (manufactured by Sysmex Corporation) was used.

4. Measurement (1) Formation of Complex

70 µL of the test substance solution and 20 µL of the capture antibody solution were mixed with each other, and reacted at 42° C. for 216 seconds. 20 µL of the labeled antibody solution was added thereto, and the mixture was reacted at 42° C. for 584 seconds to form a sandwich complex of labeled antibody-test substance-capture antibody.

(2) Immobilization of Complex on First Solid Phase

20 µL of an anti-DNP antibody solid phase suspension liquid (particle concentration: 2.5%) was added. Incubation was performed at 42° C. for 720 seconds to immobilize the complex on the solid phase. The liquid phase was removed, and washing was performed four times using 300 µL of a HISCL washing liquid (manufactured by Sysmex Corporation).

(3) Liberation of Complex

41 µL of an eluate 2 (containing 5 mM DNP-Lys, DMSO, 0.1 M MES, 2% casein Na, NaOH and NaN$_3$) was added to the solid phase with the complex immobilized thereon. By performing incubation at 42° C. for 144 seconds, the binding between the anti-DNP solid phase and the complex was broken to liberate the complex.

(4) Immobilization of Complex on Second Solid Phase

30 µL of the supernatant containing the complex was recovered, and 30 µL of a HISCL 2 reagent (manufactured by Sysmex Corporation) was added thereto. Incubation was performed at 42° C. for 288 seconds to immobilize the complex on the solid phase. The liquid phase was removed, and washing was performed four times using 300 µL of a HISCL washing liquid (manufactured by Sysmex Corporation).

(5) Enzyme Reaction and Fluorescence Measurement

50 µL of a HISCL luminescent substrate set R4 reagent (manufactured by Sysmex Corporation) and 100 µL of a HISCL luminescent substrate set R5 reagent (manufactured by Sysmex Corporation) were mixed with the solid phase with the complex immobilized thereon, the mixture was reacted at 42° C. for 300 seconds, and the luminescence intensity was measured.

(Results)

Figure 7:
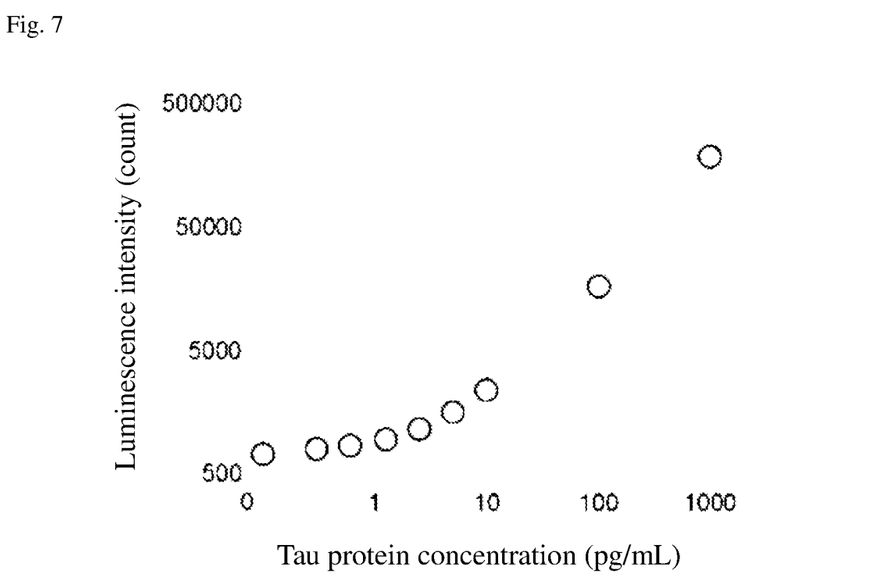
FIG. 7 is a graph showing results in Example 2.

FIG. 7 shows the fluorescence intensity measured in Example 2. The detection limit of the method in Example 2 was about 0.3 pg/mL, and the method made it possible to perform detection with a high sensitivity.

(Example 3) Detection of Amyloid β by ICT-EIA Using Capture Antibody and Labeled Antibody with Overlapping Epitopes 1. Preparation of Test Substance Solution A monomer sample containing 1000 pg/mL of an amyloid β(1-11) monomer (manufactured by Anaspec, Inc.) was prepared.

A dimer sample containing 1000 pg/mL of an amyloid β(1-16) dimer (manufactured by IBL, Inc.) was prepared.

Amyloid β42 (manufactured by IBL, Inc.) was polymerized to prepare an oligomer, and an oligomer sample containing 1000 pg/mL of the oligomer was prepared. The molecular weight of the oligomer was analyzed by gel filtration chromatography in accordance with a normal method, and the result showed that the oligomer sample had a pentameric oligomer as a main constituent component.

2. Preparation of Antibody Solution

Using an anti-amyloid β mouse monoclonal antibody (IgG) (manufactured by IBL, Inc., clone name: 82E1), a labeled antibody was prepared in the same manner as in 2. in Example 1.

Using an anti-amyloid β mouse monoclonal antibody (IgG) (manufactured by IBL, Inc., clone name: 82E1), a capture antibody was prepared in the same manner as in 2. in Example 1.

The labeled antibody solution, the capture antibody solution and the buffer solution A were mixed so as to have a labeled antibody content of 100 fmol and a capture antibody content of 100 fmol, thereby preparing 80 µL of an antibody solution.

3. Preparation of Solid Phase

An anti-DNP antibody solid phase and a STA solid phase were prepared in the same manner as in 3. in Example 2.

4. Measurement (1) Formation of Complex

70 µL of the test substance solution and 80 µL of the antibody solution were mixed with each other, and reacted at 42° C. for 92 minutes to form a sandwich complex of labeled antibody-test substance-capture antibody.

(2) Immobilization of Complex on First Solid Phase

20 µL of an anti-DNP antibody solid phase suspension liquid (particle concentration: 2.5%) was added. Incubation was performed at 42° C. for 11 minutes to immobilize the complex on the solid phase. The liquid phase was removed, and washing was performed four times using 300 µL of a HISCL washing liquid (manufactured by Sysmex Corporation).

(3) Liberation of Complex

110 µL of an eluate 2 (containing 5 mM DNP-Lys, DMSO, 0.1 M MES, 2% casein Na, NaOH and NaN$_3$) was added to the solid phase with the complex immobilized thereon. By performing incubation at 42° C. for 5 minutes, the binding between the anti-DNP solid phase and the complex was broken to liberate the complex.

(4) Immobilization of Complex on Second Solid Phase

80 µL of the supernatant containing the complex was recovered, and 30 µL of a HISCL R2 reagent (manufactured by Sysmex Corporation) was added thereto. Incubation was performed at 42° C. for 5 minutes to immobilize the complex on the solid phase. The liquid phase was removed, and washing was performed four times using 300 µL of a HISCL washing liquid (manufactured by Sysmex Corporation).

(5) Enzyme Reaction and Fluorescence Measurement

50 µL of a HISCL luminescent substrate set R4 reagent (manufactured by Sysmex Corporation) and 100 µL of a HISCL luminescent substrate set R5 reagent (manufactured by Sysmex Corporation) were mixed with the solid phase with the complex immobilized thereon, the mixture was reacted at 42° C. for 5 minutes, and the luminescence intensity was measured.

(Results)

Figure 8:
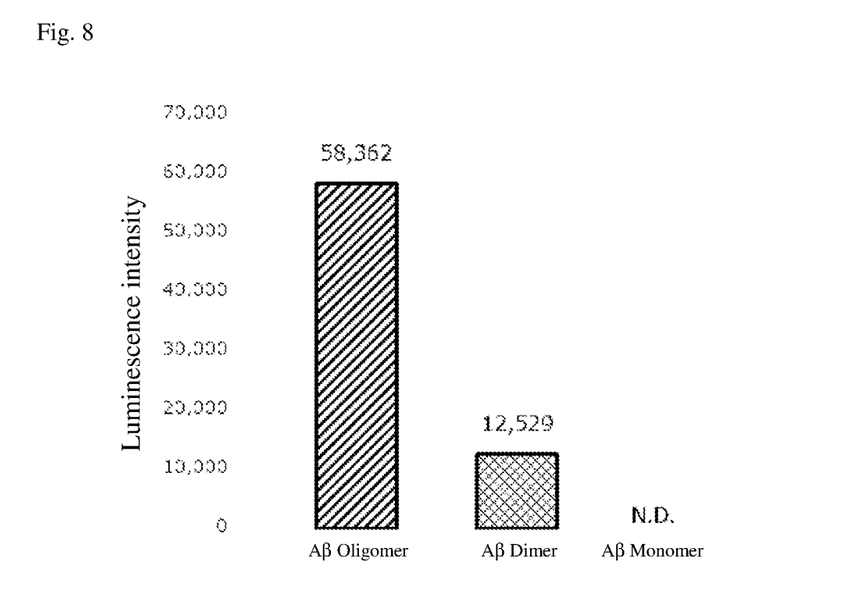
FIG. 8 is a graph showing results in Example 3.

FIG. 8 shows the fluorescence intensity measured in Example 3. An oligomer and a dimer of amyloid β (described as Aβ in the drawing) were detected, but a monomer was not detected. It was found that with the method, dimeric or higher-order amyloid β was detected, and detection of a monomer was suppressed.

(Example 4) Detection of Amyloid β by ICT-EIA Using First Capture Antibody, Second Capture Antibody and Labeled Antibody with Overlapping Epitopes 1. Preparation of Test Substance Solution A test substance solution was prepared in the same manner as in Example 3.

2. Preparation of Antibody Solution

Using an anti-amyloid β mouse monoclonal antibody (IgG) (manufactured by IBL, Inc., clone name: 82E1), a labeled antibody was prepared in the same manner as in 2. in Example 1.

Using SATA (manufactured by Thermo Fischer Scientific), a thiol group was introduced into an anti-amyloid β mouse monoclonal antibody (IgG) (manufactured by IBL, Inc., clone name: 82E1). DNP-Lys (manufactured by Tokyo Chemical Industry Co., Ltd.) was maleimidized using EMCS. The antibody, into which a thiol group had been introduced, and the maleimidized DNP-Lys were mixed with each other, and reacted to prepare a first capture antibody.

Using SATA (manufactured by Thermo Fischer Scientific), a thiol group was introduced into an anti-amyloid β mouse monoclonal antibody (IgG) (manufactured by IBL, Inc., clone name: 82E1). The antibody, into which a thiol group had been introduced, and Biotin-PEAC5-maleimide (6-{N'-[2-(N-maleimide)ethyl]-N-piperazinylamide}hexyl D-biotinamide hydrochloride) were mixed with each other, and reacted to prepare a second capture antibody.

The labeled antibody solution, the first capture antibody solution, the second capture antibody solution and the buffer solution A were mixed so as to have a labeled antibody content of 100 fmol and a first capture antibody content of 50 fmol and a second capture antibody of 50 fmol, thereby preparing 80 µL of an antibody solution.

3. Preparation of Solid Phase

An anti-DNP antibody solid phase and a STA solid phase were prepared in the same manner as in 3. in Example 2.

4. Measurement

The luminescence intensity was measured in the same manner as in Example 3.

(Results)

Figure 9:
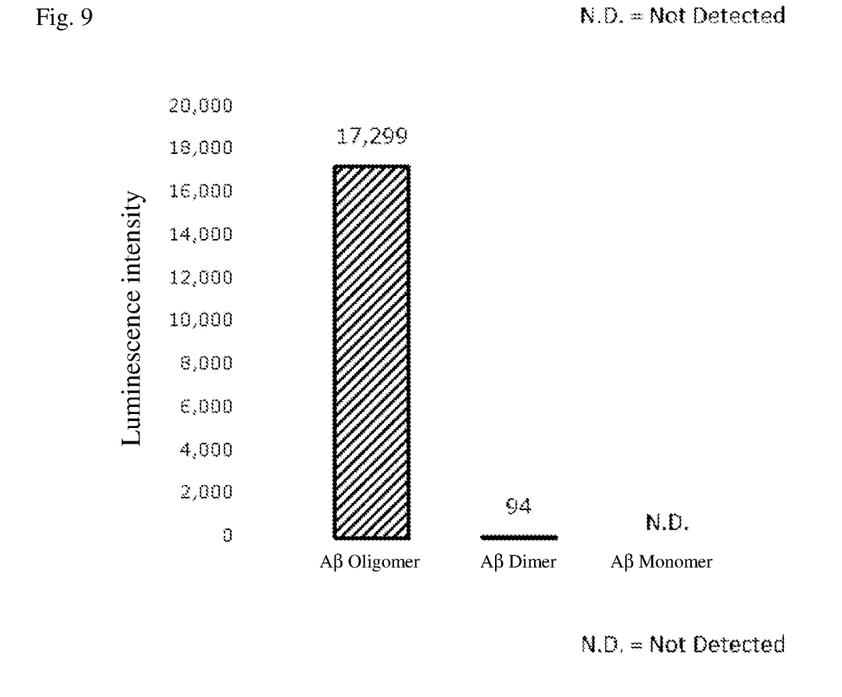
FIG. 9 is a graph showing results in Example 4.

FIG. 9 shows the fluorescence intensity measured in Example 4. Strong luminescence was detected from the oligomer sample of amyloid β (described as Aβ in the drawing). Slight luminescence was detected from the dimer sample. Luminescence was not detected from the monomer sample. It was found that with method, pentameric or higher-order amyloid β was detected, and detection of a dimer and a monomer was suppressed.

(Example 5) Detection of Tau Protein by ICT-EIA Using Capture Antibody and Labeled Antibody with Overlapping Epitopes 1. Preparation of Test Substance Solution A monomer sample containing 1000 pg/mL of a tau protein monomer (manufactured by Nipro Corporation) was prepared.

A tau protein monomer (manufactured by Wako Company) was polymerized to prepare an oligomer, and an oligomer sample containing 1000 pg/mL of the oligomer was prepared. The molecular weight of the oligomer was analyzed by gel filtration chromatography in accordance with a normal method, and the result showed that the oligomer sample had a decameric oligomer as a main constituent component.

2. Preparation of Antibody Solution

A labeled antibody was prepared in the same manner as in 2. in Example 2.

Using an anti-tau protein mouse monoclonal antibody (manufactured by BioLegend, IgG, clone name: Tau12), a capture antibody was prepared in the same manner as in 2. in Example 1.

The labeled antibody solution, the capture antibody solution and the buffer solution A were mixed so as to have a labeled antibody content of 100 fmol and a capture antibody content of 100 fmol, thereby preparing 80 µL of an antibody solution.

3. Preparation of Solid Phase

An anti-DNP antibody solid phase and a STA solid phase were prepared in the same manner as in 3. in Example 2.

4. Measurement (1) Formation of Complex

70 µL of the test substance solution and 80 µL of the antibody solution were mixed with each other, and reacted at 37° C. for 27 minutes to form a sandwich complex of labeled antibody-test substance-capture antibody.

(2) Immobilization of Complex on First Solid Phase

20 µL of an anti-DNP antibody solid phase suspension liquid (particle concentration: 2.5%) was added. Incubation was performed at 37° C. for 11 minutes to immobilize the complex on the solid phase. The liquid phase was removed, and washing was performed four times using 300 µL of a HISCL washing liquid (manufactured by Sysmex Corporation).

(3) Liberation of Complex

110 µL of an eluate 2 (containing 5 mM DNP-Lys, DMSO, 0.1 M MES, 2% casein Na, NaOH and $NaN_3$) was added to the solid phase with the complex immobilized thereon. By performing incubation at 37° C. for 5 minutes, the binding between the anti-DNP solid phase and the complex was broken to liberate the complex.

(4) Immobilization of Complex on Second Solid Phase

80 µL of the supernatant containing the complex was recovered, and 30 µL of a suspension liquid (particle concentration: 2.5%) of the STA solid phase was added thereto. Incubation was performed at 37° C. for 5 minutes to immobilize the complex on the solid phase. The liquid phase was removed, and washing was performed four times using 300 µL of a HISCL washing liquid (manufactured by Sysmex Corporation).

(5) Enzyme Reaction and Fluorescence Measurement

50 µL of a HISCL luminescent substrate set R4 reagent (manufactured by Sysmex Corporation) and 100 µL of a HISCL luminescent substrate set R5 reagent (manufactured by Sysmex Corporation) were mixed with the solid phase with the complex immobilized thereon, the mixture was reacted at 42° C. for 5 minutes, and the luminescence intensity was measured.

(Results)

Figure 10:
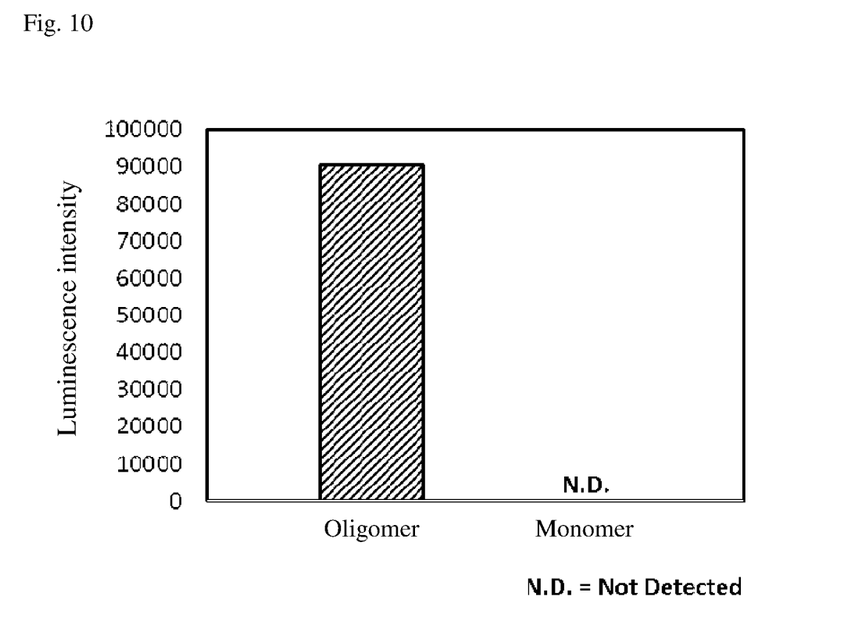
FIG. 10 is a graph showing results in Example 5.

FIG. 10 shows the fluorescence intensity measured in Example 5. An oligomer of tau protein was detected, but a monomer of tau protein was not detected. It was found that with the method, a tau protein oligomer was detected, and detection of a monomer was suppressed.

REFERENCE SIGNS LIST

30: Reagent kit
31: First container
32: Second container
33: Third container
34: Fourth container
37: Attached document
38: Packing box
40: Reagent kit
41: First container
42: Second container
43: Third container
44: Fourth container
45: Fifth container
47: Attached document
48: Packing box

The invention claimed is:

1. A method for detecting a test substance, the method comprising the steps of:
    forming on a first solid phase a complex comprising a test substance, a labeled antibody, a first capture antibody and a second capture antibody by bringing the test substance, the labeled antibody, the first capture antibody, the second capture antibody and the first solid phase into contact with one another wherein the labeled antibody is bound to the test substance, the first capture antibody is bound to the test substance, the second capture antibody is bound to the test substance, and the first solid phase is bound to the first capture antibody;
    transferring the complex onto a second solid phase by breaking the binding between the first capture antibody and the first solid phase to liberate the complex, and bringing the second solid phase and the complex into contact with each other, wherein the second solid phase is bound to the second capture antibody; and
    detecting the test substance by measuring a label contained in the complex on the second solid phase, wherein
    the test substance is a trimeric or higher-order multimer, and
    an epitope for the labeled antibody, an epitope for the first capture antibody and an epitope for the second capture antibody overlap one another.

2. The method according to claim 1, wherein the test substance comprises a polypeptide.

3. The method according to claim 1, wherein the test substance is amyloid β or tau protein.

4. The method according to a claim 1, wherein
    the first capture antibody comprises a first binding substance, and the first solid phase comprises a first binding partner that is bound specifically to the first binding substance,
    the first binding partner and the first binding substance are bound specifically to each other to bind the complex onto the first solid phase in the formation step,
    the second capture antibody comprises a second binding substance, and the second solid phase comprises a second binding partner that is bound specifically to the second binding substance, and
    the second binding partner and the second binding substance are bound specifically to each other to bind the liberated complex to the second solid phase in the transfer step.

5. The method according to claim 1, wherein
    the first solid phase is in the form of particles, and
    the method comprises the step of removing unreacted components, and recovering the first solid phase after the formation step and before the transfer step.

6. The method according to claim 1, wherein the complex on the first phase is liberated from the first solid phase by a releasing agent in the transfer step.

7. The method according to claim 1, wherein the method comprises the step of removing unreacted components, and recovering the second solid phase after the transfer step and before the detection step.

8. The method according to claim 4, wherein the first binding partner is an anti-hapten antibody, the first binding substance is a hapten, the second binding partner is an avidin, and the second binding substance is a biotin.

9. The method according to claim 8, wherein
    the hapten is a dinitrophenyl group, and
    the complex on the first solid phase is liberated from the first solid phase using a dinitrophenyl amino acid in the transfer step.

10. The method according to claim 1, wherein the label is an enzyme or a fluorescent substance.

11. The method according to claim 1, wherein
    the label is β-galactosidase or alkaline phosphatase, and
    in the measurement step, a substrate of the enzyme is reacted with the enzyme, and a label generated from a reaction product produced by the enzyme reaction is measured.

12. The method according to claim 1, wherein
    the label is a fluorescent substance, and
    in the measurement step, the complex on the second solid phase is irradiated with excitation light, and fluorescence generated from the label of the complex is measured.

13. A method for detecting a test substance, comprising:
    conducting an immune complex transfer enzyme immunoassay (ICT-EIA) using a labeled antibody, a first capture antibody and a second capture antibody to detect the test substance, wherein
    the labeled antibody is bound to the test substance, the first capture antibody is bound to the test substance, the second capture antibody is bound to the test substance, and the first solid phase is bound to the first capture antibody,
    the test substance is a trimeric or higher-order multimer, and
    an epitope for the labeled antibody, an epitope for the first capture antibody and an epitope for the second capture antibody overlap one another.

14. The method according to claim 13, wherein the test substance comprises a polypeptide.

15. The method according to claim 13, wherein the test substance is amyloid β or tau protein.

* * * * *